US009599544B2

(12) United States Patent
Hart et al.

(10) Patent No.: US 9,599,544 B2
(45) Date of Patent: Mar. 21, 2017

(54) METHOD AND APPARATUS FOR PREPARING A BALE SAMPLE FROM A BALE OF FIBROUS MATERIAL, AND A BALE SAMPLE PRODUCED THEREBY

(71) Applicant: LANGSTON COMPANIES INC., Memphis, TN (US)

(72) Inventors: Joseph Harold Hart, Bakersfield, CA (US); Anton G. Holty, Bakersfield, CA (US); Edward D. Mayer, Bakersfield, CA (US)

(73) Assignee: LANGSTON COMPANIES INC., Memphis, TN (US)

( * ) Notice: Subject to any disclaimer, the term of this patent is extended or adjusted under 35 U.S.C. 154(b) by 510 days.

(21) Appl. No.: 14/138,327

(22) Filed: Dec. 23, 2013

(65) Prior Publication Data

US 2014/0174209 A1   Jun. 26, 2014

Related U.S. Application Data

(60) Provisional application No. 61/740,701, filed on Dec. 21, 2012.

(51) Int. Cl.
| *G01N 1/28* | (2006.01) |
| *G01N 1/04* | (2006.01) |
| *G01N 33/36* | (2006.01) |
| *G01N 35/00* | (2006.01) |
| *G01N 1/00* | (2006.01) |

(52) U.S. Cl.
CPC ............. *G01N 1/286* (2013.01); *G01N 1/04* (2013.01); *G01N 33/362* (2013.01); *G01N 35/00732* (2013.01); *G01N 2001/005* (2013.01)

(58) Field of Classification Search
CPC ....................................................... G01N 1/286
USPC ......................................................... 73/864.41
See application file for complete search history.

(56) References Cited

U.S. PATENT DOCUMENTS

| 586,065 | A | 7/1897 | Robinson |
| 1,960,137 | A | 5/1934 | Brown |
| 2,131,502 | A | 9/1938 | Elliot |
| 2,459,383 | A | 1/1949 | Levy |

(Continued)

FOREIGN PATENT DOCUMENTS

| DE | 8616467 U1 | 7/1986 |
| EP | 1044825 A1 | 10/2000 |

(Continued)

OTHER PUBLICATIONS

International Search Report from Corresponding PCT Application No. PCT/US2013/077398, mailed Apr. 15, 2014.

(Continued)

*Primary Examiner* — Clayton E Laballe
*Assistant Examiner* — Dennis Hancock
(74) *Attorney, Agent, or Firm* — Workman Nydegger

(57) ABSTRACT

A method for preparing a bale sample, a bale sampling apparatus, and a bale sample are provided. The method includes the steps of removing a portion from a bale of fibrous material and wrapping an elongated substrate completely around the portion to form a bale sample. The elongated substrate includes identification information. The identification information includes information that associates the bale sample with the bale of fibrous material.

17 Claims, 18 Drawing Sheets

(56) References Cited

U.S. PATENT DOCUMENTS

| | | |
|---|---|---|
| 2,607,711 A | 8/1952 | Hendricks |
| 2,829,073 A | 4/1958 | Williams |
| 2,880,862 A | 4/1959 | Sermattei |
| 3,034,358 A | 5/1962 | Young et al. |
| 3,146,654 A | 9/1964 | Mathews et al. |
| 3,464,298 A | 9/1969 | Roach |
| 3,648,350 A | 3/1972 | Cassidy et al. |
| 3,850,786 A | 11/1974 | Jeffries et al. |
| 4,010,680 A | 3/1977 | Buck, Jr. et al. |
| 4,562,102 A | 12/1985 | Rabuse et al. |
| 4,770,913 A | 9/1988 | Yamamoto |
| 5,069,969 A | 12/1991 | McClintock et al. |
| 5,178,020 A | 1/1993 | Elam et al. |
| 5,182,156 A | 1/1993 | Pape et al. |
| 5,221,393 A | 6/1993 | Heutschi |
| 5,324,078 A | 6/1994 | Bane |
| 5,388,300 A | 2/1995 | Hickey |
| 5,509,256 A | 4/1996 | Groth |
| 5,520,308 A | 5/1996 | Berg, Jr. et al. |
| 5,531,061 A | 7/1996 | Peterson |
| 5,591,521 A | 1/1997 | Arakawa et al. |
| 5,817,382 A | 10/1998 | Cheng |
| 6,127,014 A | 10/2000 | McKay, Jr. |
| 6,182,418 B1 | 2/2001 | McFarland |
| 6,210,768 B1 | 4/2001 | Blok et al. |
| 6,250,495 B1 | 6/2001 | Bando |
| 6,386,026 B1 | 5/2002 | Zamfes |
| 6,787,209 B2 | 9/2004 | Mass et al. |
| 6,971,542 B2 | 12/2005 | Vogel et al. |
| 7,541,080 B2 | 6/2009 | Mass et al. |
| 8,336,404 B2 | 12/2012 | Actis |
| 2004/0115393 A1 | 6/2004 | Vogel et al. |
| 2009/0107349 A1* | 4/2009 | Noonan ................. A01F 15/071 100/14 |
| 2009/0188332 A1 | 7/2009 | Actis |
| 2009/0217827 A1* | 9/2009 | Duenwald ........... A01F 15/0715 100/88 |
| 2011/0011036 A1 | 1/2011 | Falise et al. |
| 2011/0209439 A1 | 9/2011 | Actis |
| 2013/0104675 A1 | 5/2013 | Actis |
| 2014/0096623 A1* | 4/2014 | Mansfield ................ G01N 1/04 73/863.21 |

FOREIGN PATENT DOCUMENTS

| | | |
|---|---|---|
| EP | 1321028 A1 | 6/2003 |
| GB | 2292325 A | 2/1996 |
| JP | 06-255670 A | 9/1994 |
| JP | 3046016 U | 2/1998 |
| WO | 2004/054898 A1 | 7/2004 |
| WO | 2009/094667 A1 | 7/2009 |

OTHER PUBLICATIONS

"United States Department of Agriculture, Agricultural Marketing Service, Cotton Program, Instructions to Samplers Drawing Samples for Smith-Doxey (Form 1) Classification", as of Dec. 21, 2012.

* cited by examiner

METHOD AND APPARATUS FOR PREPARING A BALE SAMPLE FROM A BALE OF FIBROUS MATERIAL, AND A BALE SAMPLE PRODUCED THEREBY

FIELD OF THE DISCLOSURE

The present disclosure relates to a method for preparing a sample from a bale of fibrous material by wrapping identification information completely around the sample, apparatus for producing the sample and the resulting sample.

BACKGROUND

Samples are taken from a bale of agricultural products, for example, cotton or other fibrous materials, so that the sample can be analyzed by an agency, typically a division of the U.S. Department of Agriculture (USDA). Currently, the USDA requires that a ID tag be put between the two half's of the sample, one portion from each side of the bale. The sample with the tag is then rolled or put into a heavy paper sleeve the length of the sample. The sample must be conditioned for moisture and temperature before grading. The heavy sleeve must be removed before this can be done. The rolled sample must be unrolled before this can be done. (See, for example, "Instructions to Samplers Drawing Samples for Smith-Doxey (Form 1) Classification," published in association with the USDA Agriculture Marketing Service Cotton Program.) The sample is analyzed for density, moisture content, and other classifying information in order to classify and grade the bale for shipment and delivery.

The sample taken from the bale is typically formed during the bale pressing and bagging process in the ginning mill by cutting the bale on at least two sides, e.g., the top and bottom of the bale, during the bale pressing process. The bale is then rotated to expose the two cut portions on what is now each side of the bale, and individual sections of the bale are removed to be combined, and further processed to form a sample and shipped to the certifying agency. During the bale bagging process, the cut portions on each side are removed at a sampling station by grasping and pulling the cut portions to form the sample of the bale before bagging. After the bale is bagged at a bagging station, identification information in the form of a Permanent Bale Identification (PBI) tag having a unique optically readable number and standard scannable barcode is permanently attached to the bagged bale at a labeling station, which is used to identify the bale based on the gin code/gin bale number, for example, in a 12-digit coding that complies with the USDA standards for identifying cotton bales.

In a known manner, the combined sample taken from the bale is identified with the bale by placing a USDA-AMS Cotton Identification Coupon, which is printed with and removed from the bale's PBI tag, between the inside surfaces of the two sample sections. The sample is then placed in a bag with other samples and delivered to the USDA for classification and grading. In this process, however, the samples tend to unwind or unroll when placed in the bag and during delivery of the bag, so that the identification coupon becomes misplaced or separated from the sample.

In another exemplary known sampling processes, as described in U.S. publication 2009/0188332, filed Jan. 26, 2009, a set of grippers is used to remove the cut portions of the bale. The cut portion are then combined into a single sample and bagged in a sample bag which is sent to the USDA for analysis. At the classifying office, however, typically the samples are removed from the bags in which they arrive in order for the sample to be laid out for classifying and grading by conditioning the sample in a temperature and humidity controlled room. The identification information on the bag can then be misplaced or separated from the sample by, for example, and lost.

There is a need in the art for a method for efficiently preparing a cotton bale sample that has identification information securely fastened to the cotton bale sample during shipping, classification and grading to prevent the separation of the identification information from the sample while at the same time maintaining the integrity of the sample.

SUMMARY

The present disclosure concerns wrapping a cotton bale sample with an elongate substrate (for example, a band) having identification information thereon completely around the cotton bale sample to identify the sample with the compressed bale of cotton from which the sample was taken. By wrapping the cotton bale sample with the substrate fastened at its opposed ends and having the identification information, the separation of the identification information from the sample is prevented and the integrity of the sample is preserved. The band can then be used as an information coupon until the sample is discarded.

To this end, a method for preparing a cotton bale sample, a cotton bale sampling apparatus, and a cotton bale sample are disclosed. The cotton bale method includes the steps of removing a portion of cotton from a cotton bale and wrapping an elongated substrate completely around the portion of cotton to form a cotton bale sample.

The cotton bale sampling apparatus includes a portion removing device configured to remove a portion of cotton from a cotton bale and a wrapping station configured to wrap an elongated substrate around the portion of cotton to form a cotton bale sample.

The cotton bale sample includes at least one portion of cotton removed from a cotton bale and an elongate substrate wrapped around the portion of cotton to form the cotton bale sample.

In the method for preparing the cotton bale sample, the cotton bale sampling apparatus, and the cotton bale sample, the elongated substrate includes identification information associating the cotton bale sample with the cotton bale. The elongate substrate has identification that may include a scannable bar code and/or unique eye or optical readable bale identifier to assist an associate to sample the bale from which the sample was taken.

BRIEF DESCRIPTION OF THE DRAWINGS

Exemplary methods and apparatus for producing a cotton bale sample and resulting embodiments of a bale sample will be apparent from the following description and the drawings appended hereto.

Figure 1:
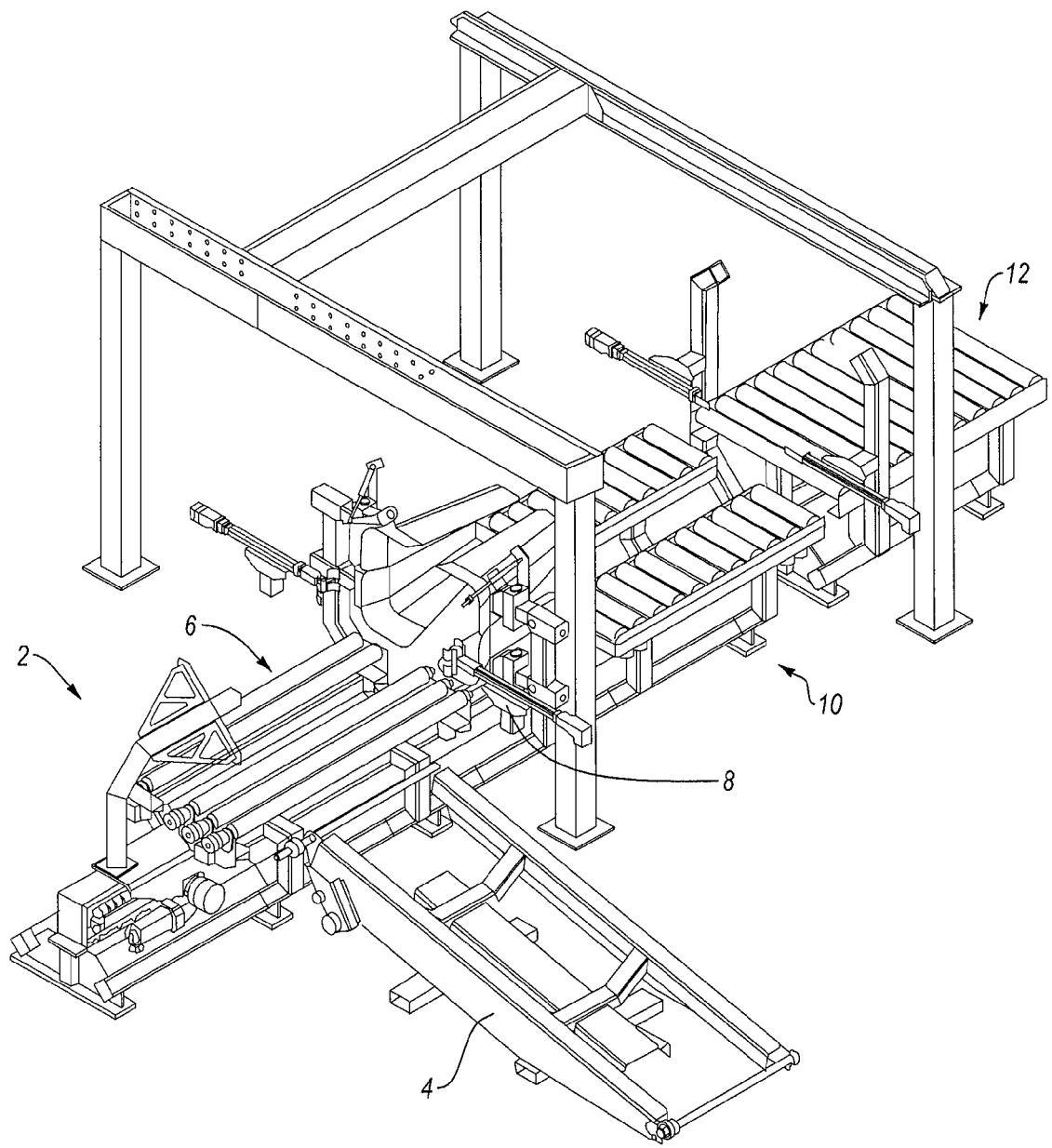
FIG. 1 is a right side isometric view of a bale bagging apparatus showing the sections of the bale bagging apparatus.

In the various figures, similar reference numbers are used for similar elements. It should be noted that the drawing figures are not necessarily drawn to any scale, or proportion, but instead are drawn to provide an understanding of the disclosure. Thus, the illustrations are not intended to be limiting as to the scope of the invention described herein, but rather to provide exemplary illustrations thereof.

DETAILED DESCRIPTION OF VARIOUS EMBODIMENTS

A. Discussion of Various Embodiments

As generally discussed above, the prior art cotton bale sample collecting devices are not designed to effectively maintain, i.e., secure, the cotton bale sample identification information with the bale sample during classifying and grading the cotton bale sample at the USDA offices. To overcome this shortcoming, the present invention was developed to provide a more secure system for fastening the identification information to the cotton bale sample by wrapping an elongate substrate such as a band having identification information completely around the sample.

The present disclosure is concerned with wrapping a cotton bale sample with an elongate substrate (e.g., a band) having identification information thereon completely around the cotton bale sample to identify the sample with the compressed bale of cotton from which the sample was taken. By wrapping the cotton bale sample with the substrate fastened at its opposed ends and having the identification information, the separation of the identification information from the sample is prevented and the integrity of the sample is preserved or maintained until the band is removed. The band can then be utilized as a sample information coupon until discarded.

To this end, an inventive method for preparing the cotton bale sample is provided by removing at least one cut portion from a compressed bale of cotton to form a cotton bale sample section and wrapping an elongate substrate having identification information completely around the cotton bale sample sections to form a cotton bale sample and fastening the opposed ends of the band together, where the identification information includes at least information to associate the cotton bale sample with the compressed bale of cotton.

Further, the method may include a step of rolling and at least partially compacting the collected cotton bale sample before applying the substrate (band) to the sample to facilitate the wrapping of the substrate completely around the sample and to ensure that the elongate substrate is held on the sample by the cotton material as it springs out upon being released from compaction.

Still further, the elongate substrate has identification information includes a scannable bar code and unique eye or optical readable bale identifier to associate the sample to the bale from which the sample was taken.

With reference to FIG. 1, a layout of a bale bagging apparatus 2 is shown to illustrate the environment in which the method for preparing a cotton bale sample having identification information wrapped completely around the sample is operated. The bale bagging apparatus 2 includes a bale feeding station, where a cotton bale is loaded on the bale bagging apparatus from a bale feeder 4. As discussed above, the cotton bale after the pressing process typically has at least two portions on opposite sides of the bale that have been cut. A conveyor 6 or system configured to push the cotton bale is then used to move the bale having the at least two cut portions along a longitudinal axis of the bale bagging apparatus 2 from a sampling station 8 to a bagging station 10, and then to a labeling station 12.

Before the cotton bale is bagged at a bagging station 10, the at least two cut portions of the bale are removed at the sampling station 8 to form a sample of the cotton bale. After the cotton bale is bagged at a bagging station 10, identification information in the form of a Permanent Bale Identification (PBI) tag having a unique eye readable number and standard scannable or machine-readable barcode is permanently attached to the bagged cotton bale at a labeling station 12, which is used to identify the bale based on the gin code/gin bale number, for example, in a 12-digit coding and comply with the USDA standards for identifying cotton bales during transportation and delivery.

Figure 2:
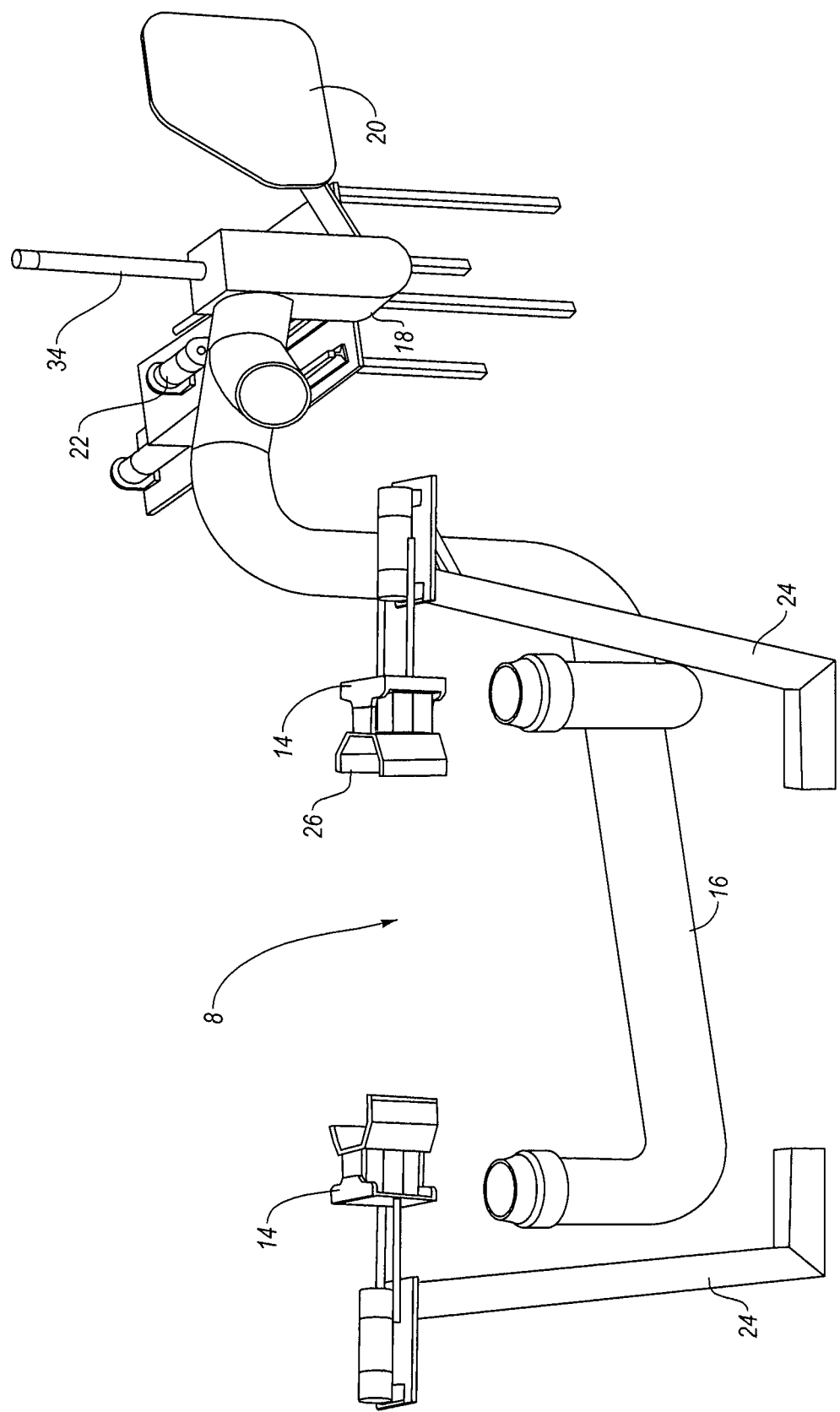
FIG. 2 is a right side isometric view of one embodiment of a sampling station having grippers, a pneumatic transport system, collection device, printing station, and compacting device.
Figure 3:
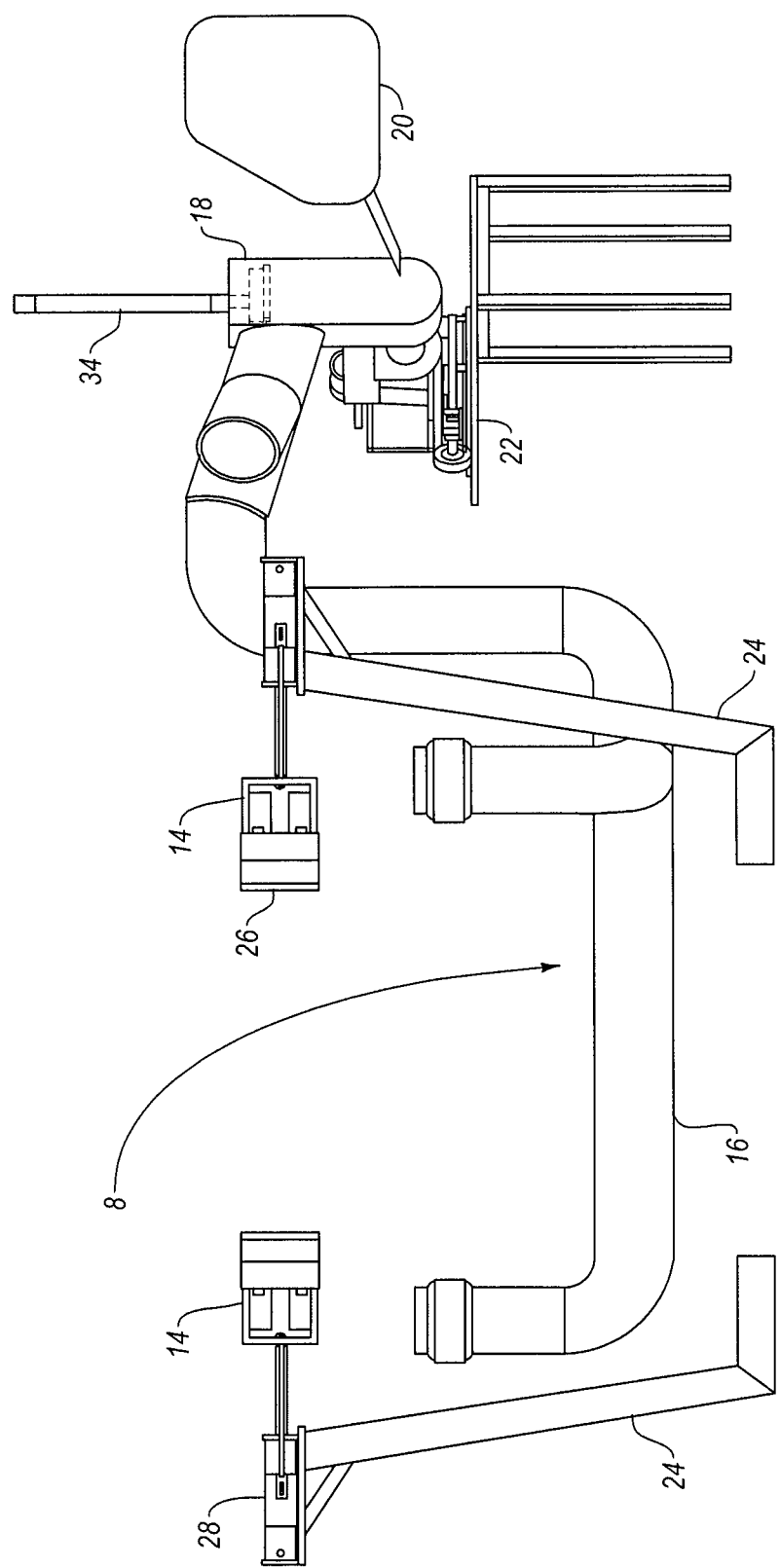
FIG. 3 is a front view of the sampling station as illustrated in FIG. 2.

One embodiment of an apparatus used to prepare a cotton bale sample having identification information wrapped around the sample is illustrated in FIGS. 2 and 3. In this embodiment of the present disclosure, the bale sampling station 8 is connected with the bale bagging apparatus 2, where the bale sampling station 8 includes a pair of grippers 14 on opposite sides of the sampling station 8, a vacuum or pneumatic transport system 16 located below each pair of grippers 14, a collection device 18 connected to the pneumatic transport system, a printing station 20, and a compacting device 22 configured to engage and disengage with the collection device 18. More specifically, the bale sampling station 8 is configured to obtain at least one sample section from the cotton bale, preferably at least two sample sections from each side of the cotton bale, where the sample sections are removable from the pre-cut portions of the cotton bale after the bale pressing process, as known in the art. Typically, the sampling station 8 is located before the bagging station 10 to allow the taking of a sample section before the cotton bale is bagged. It is to be appreciated that the sampling station 8, however, can be located anywhere along the bale processing system.

With reference to FIGS. 2 and 3, the bale sampling station 8 has a support frame 24 that is configured to be connected with the bale bagging apparatus 2. The support frame 24 includes solid or hollow beams that can be fastened using screws, bolts, or other fastening devices for securement to the base frame of the bale bagging apparatus 2. The support frames 24 are also configured to support at least two grippers 14 which are located on opposite sides of the conveyor 6 so that each gripper 14 is positioned to engage and remove the at least one cut portion from the sides of the bale to obtain a sample of the bale, which will be used for classifying and grading.

The grippers 14 include gripper jaws 26 that are configured to open and close to grab and release the sample sections from the bale. In this embodiment, a gripper actuator 28 is used to affect the operation of the positioning and opening and closing of the gripper jaws 26, where the actuator 28 is driven electrically, pneumatically, or hydraulically. The skilled person, however, would appreciate that other known devices can also be used for obtaining the sample from the bale, where the gripping device allows the opening, closing, and positioning of the grippers 14 for grabbing and removing the cut portions from the cotton bale.

Figure 4:
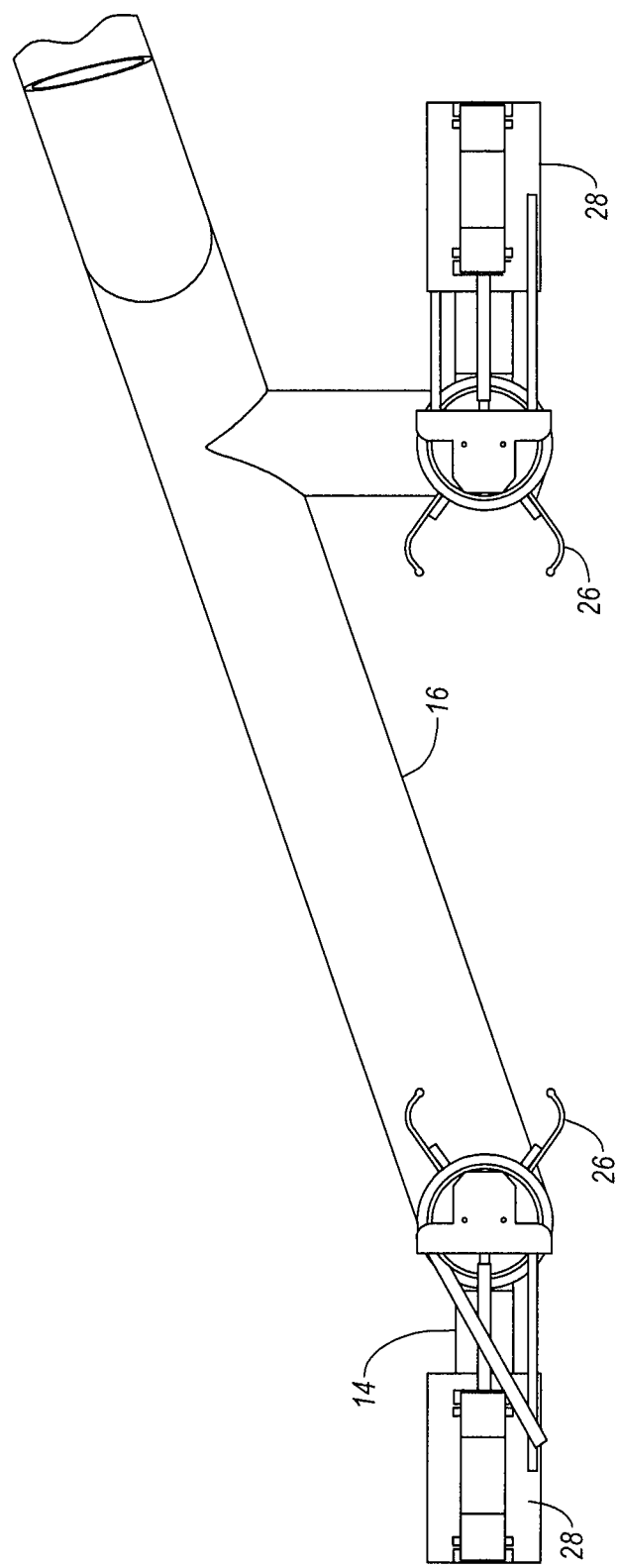
FIG. 4 is a top side view of the grippers and pneumatic transport system of FIG. 2.

As seen in FIG. 4, not only are the grippers 14 used for removing the cotton bale sample sections from the cotton bale, the grippers 14 are also configured and positioned to deposit, e.g., drop, the sample sections in the pneumatic transport system 16 once the sample sections have been removed from the bale. Once the cotton bale sample sections are taken from the cotton bale and deposited by the grippers 14 into the pneumatic transport system 16, the pneumatic transport system 16 has a pipe section which is used to transport the sample sections to a collection device 18 using a vacuum pump (not shown) or pneumatic conveying system that is connected to the collection device 18 and pneumatic transport system 16. The vacuum pump may be mounted to the intake of a transport tube, which would cause the removed sample to be pushed into a collecting unit. Or a vacuum pump may be mounted on the discharge end of the transport tube, causing the sample to be pulled through a transport tube. The vacuum or pneumatic transport system 16 is preferably formed of a light weight, high strength metal, plastic, or PVC that is vacuum rated.

Figure 5:
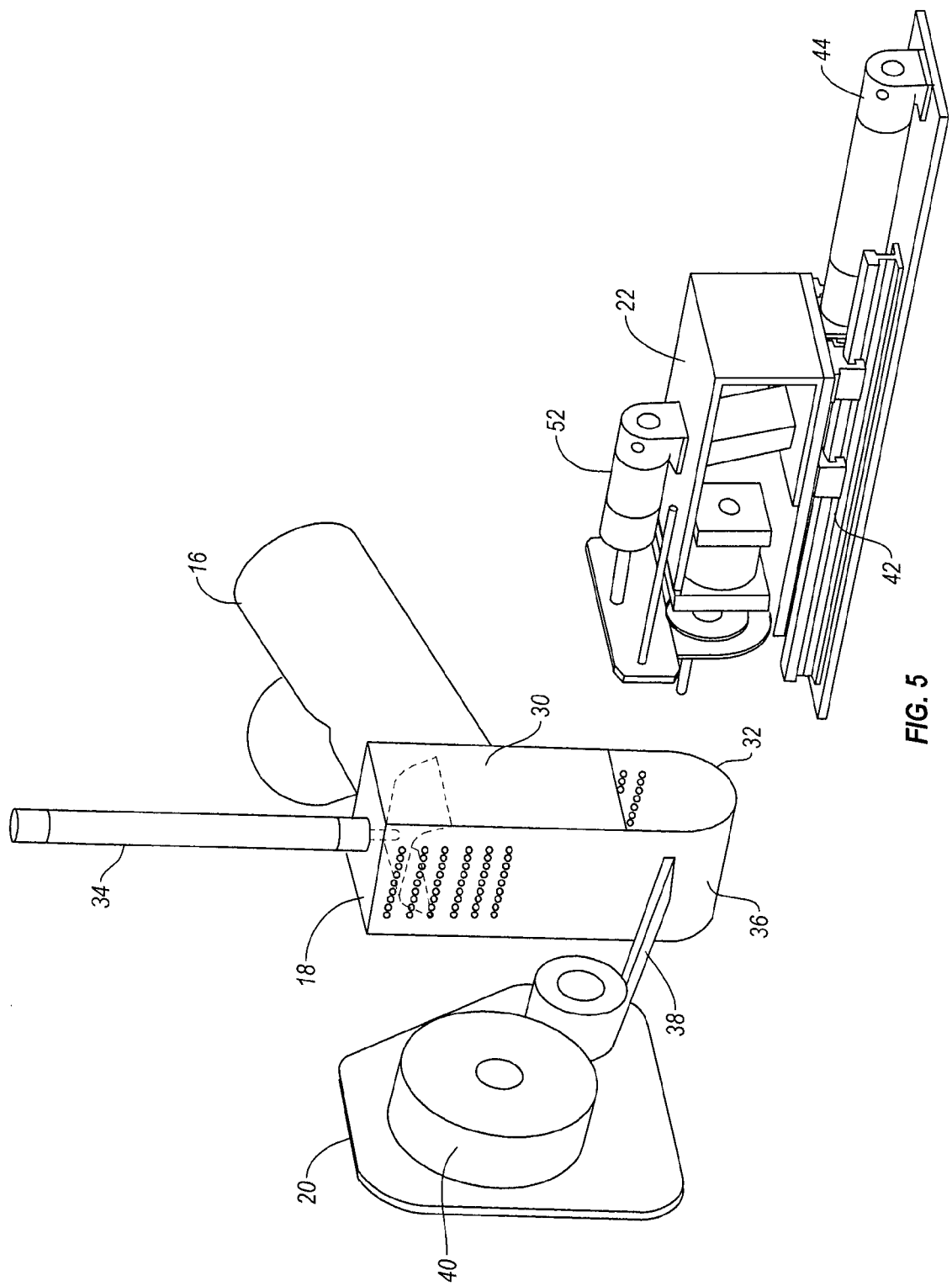
FIG. 5 is a left side isometric view of the collection device, printing station, and compacting device of the sampling station illustrated in FIG. 2.
Figure 6:
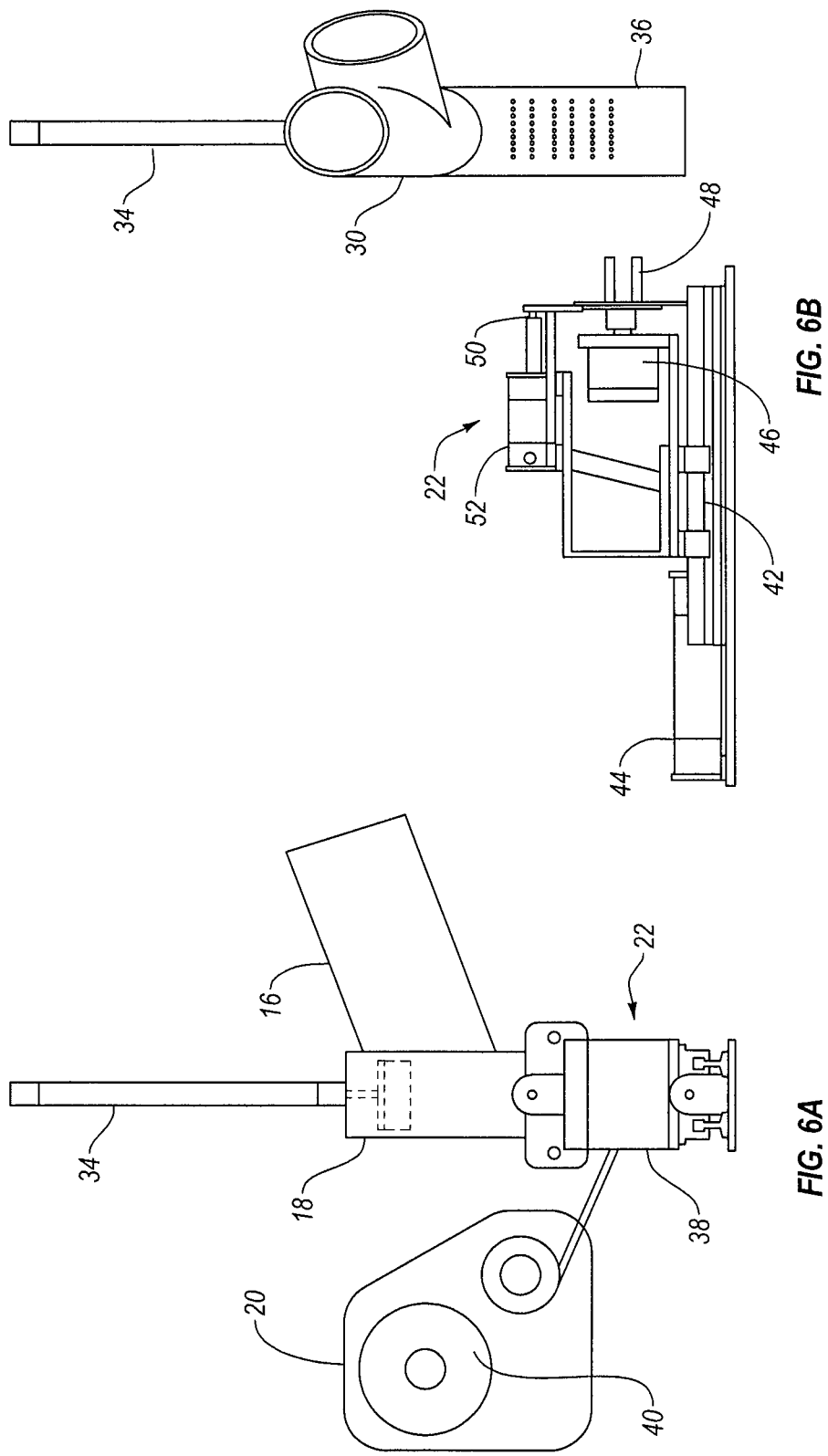
FIG. 6(a) is a front view of the collection device, printing station, and compacting device of the sampling station illustrated in FIG. 2.
FIG. 6(b) is a right side view of the collection device and compacting device of the sampling station illustrated in FIG. 2.

As illustrated in FIGS. 5-6(*b*), the collection device 18 has a first opening 30 for receiving the sample sections from the pneumatic transport system and a second opening 32 below the first opening configured to engage the compacting device 22. A plunger 34 is provided on an upper portion of the collection device 18 above the first opening 30, so that the plunger 34 pushes the cotton bale sample sections to a curved portion 36 of the collection device 18. The plunger 34 can optionally be provided with a curved foot that is configured to engage the cotton bale sample sections in the collection device 18. The curved portion 36 is located at a bottom section of the collection device 18 next to the second opening 32 and is arranged to facilitate the rolling of the bale sample sections when the compacting device 22 is engaged with the collection device through the second opening 32.

Figure 10:
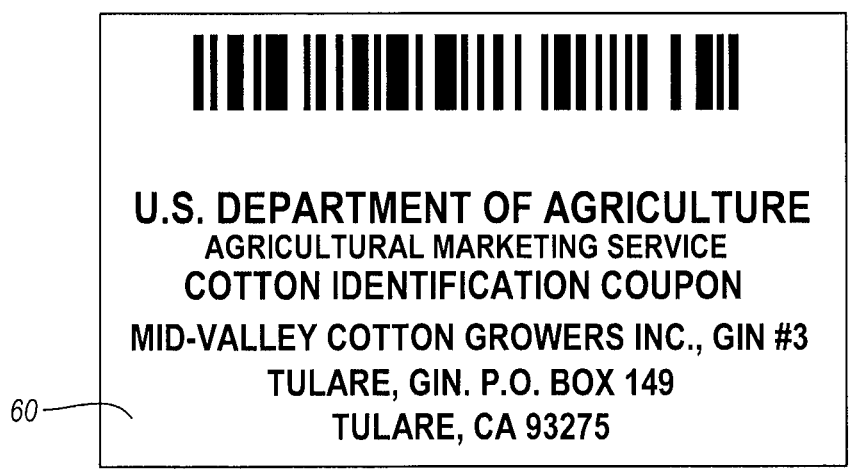
FIG. 10 shows identification information printed on a label used with this embodiment.
Figure 11:
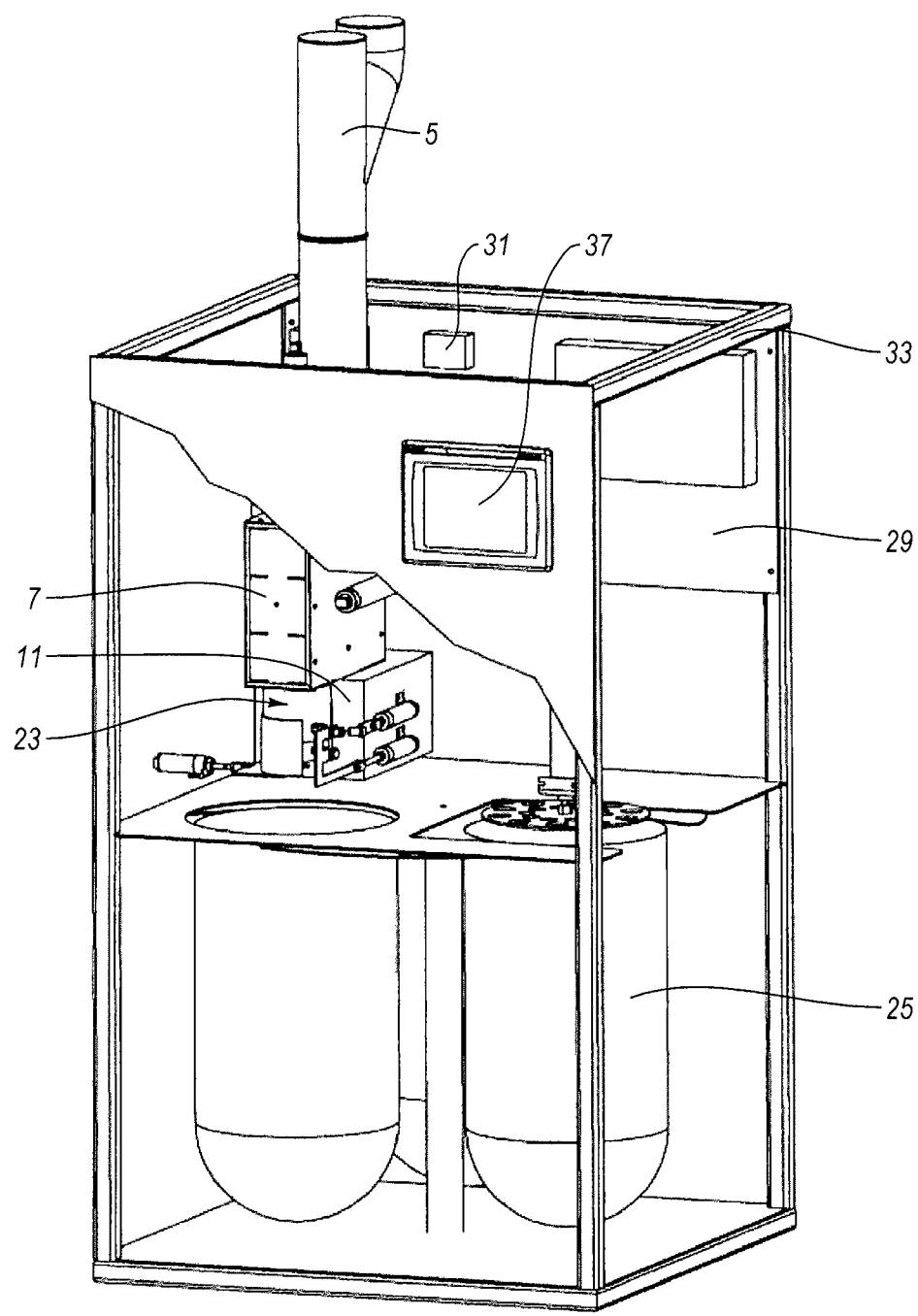
FIG. 11 shows a right side isometric view of a cotton sample wrapping apparatus according to another embodiment.
Figure 12:
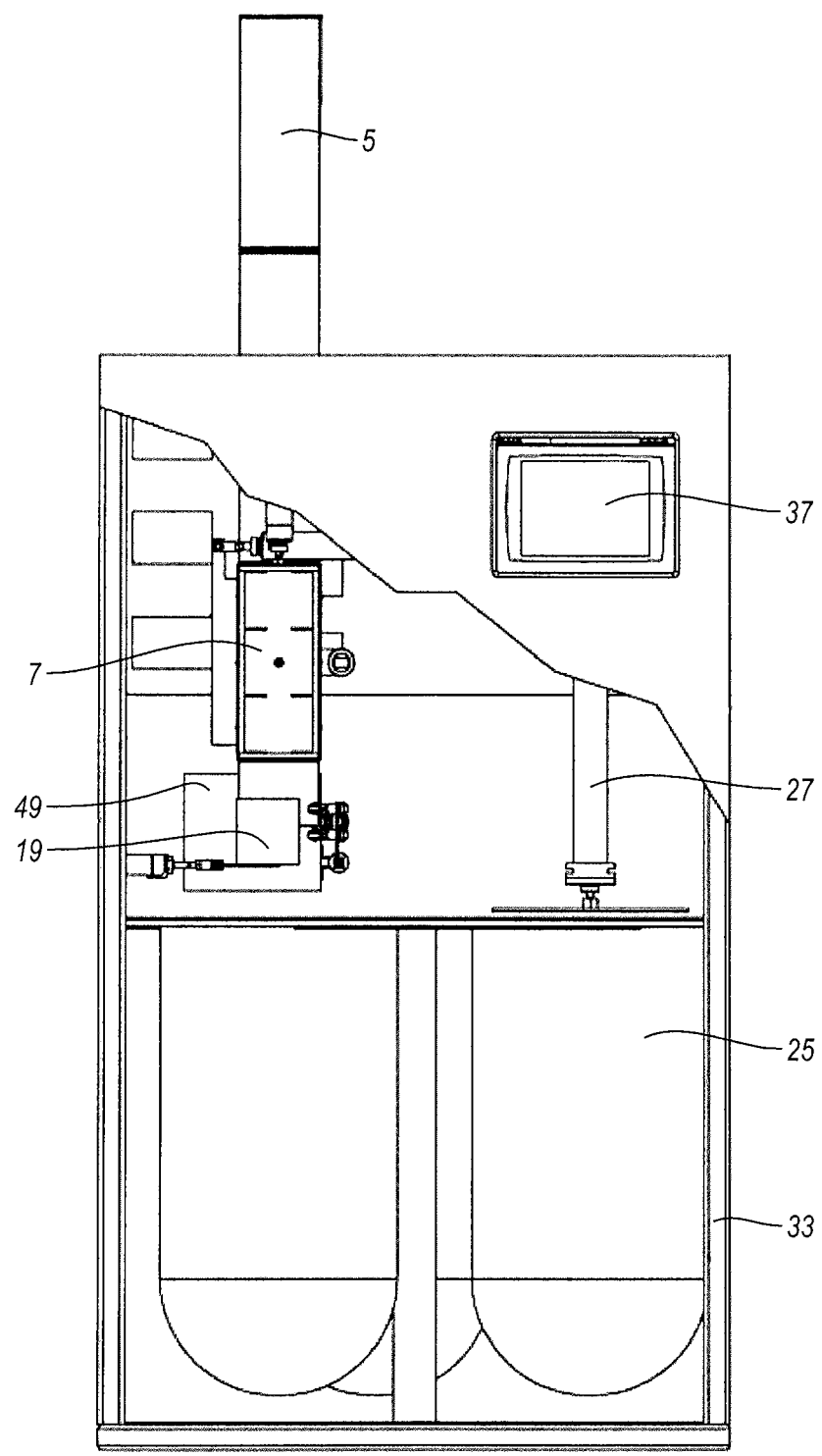
FIG. 12 shows a front elevation view of the cotton sample wrapping apparatus according to the other embodiment.
Figure 13:
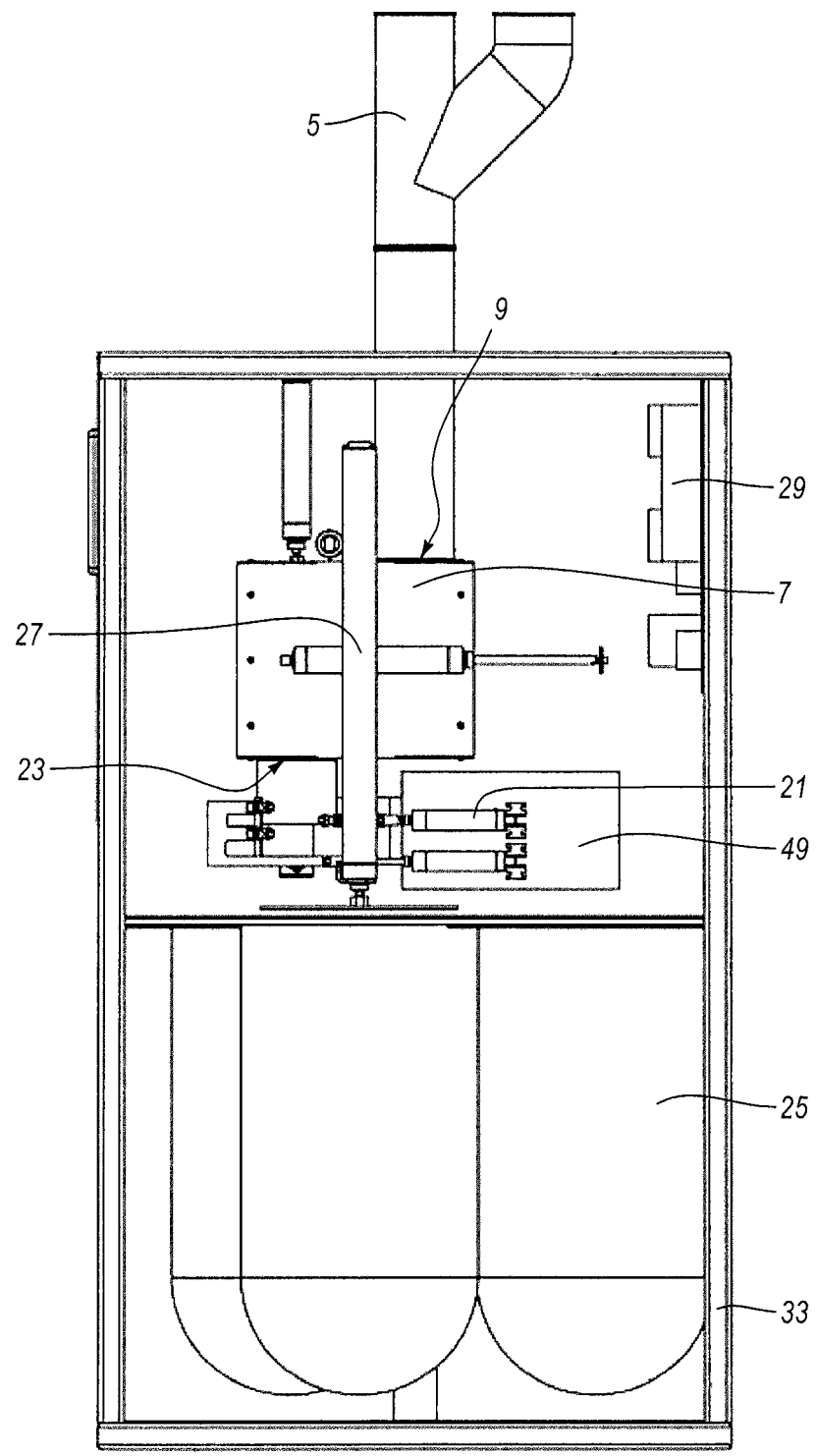
FIG. 13 shows a right side elevation view of the cotton sample wrapping apparatus according to the other embodiment.
Figure 14:
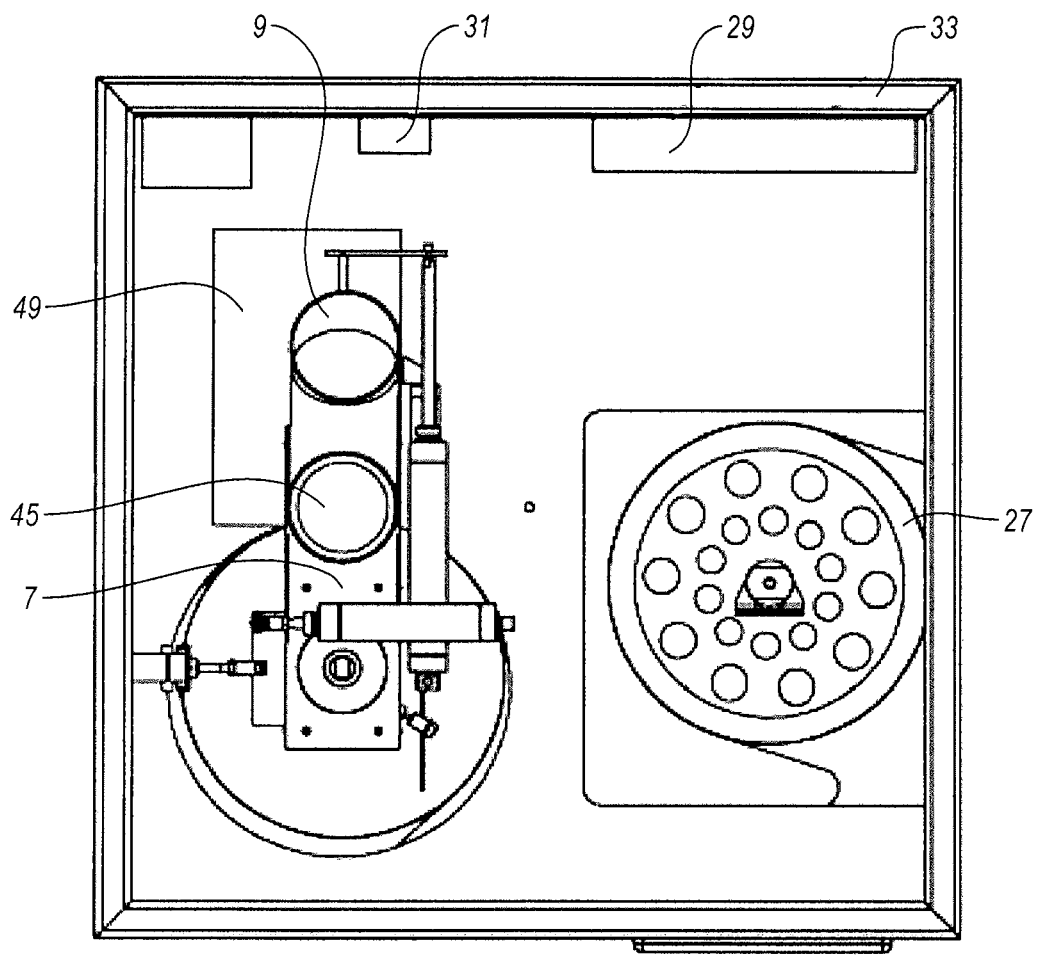
FIG. 14 shows a top view of the cotton sample wrapping apparatus according to the other embodiment.
Figure 15:
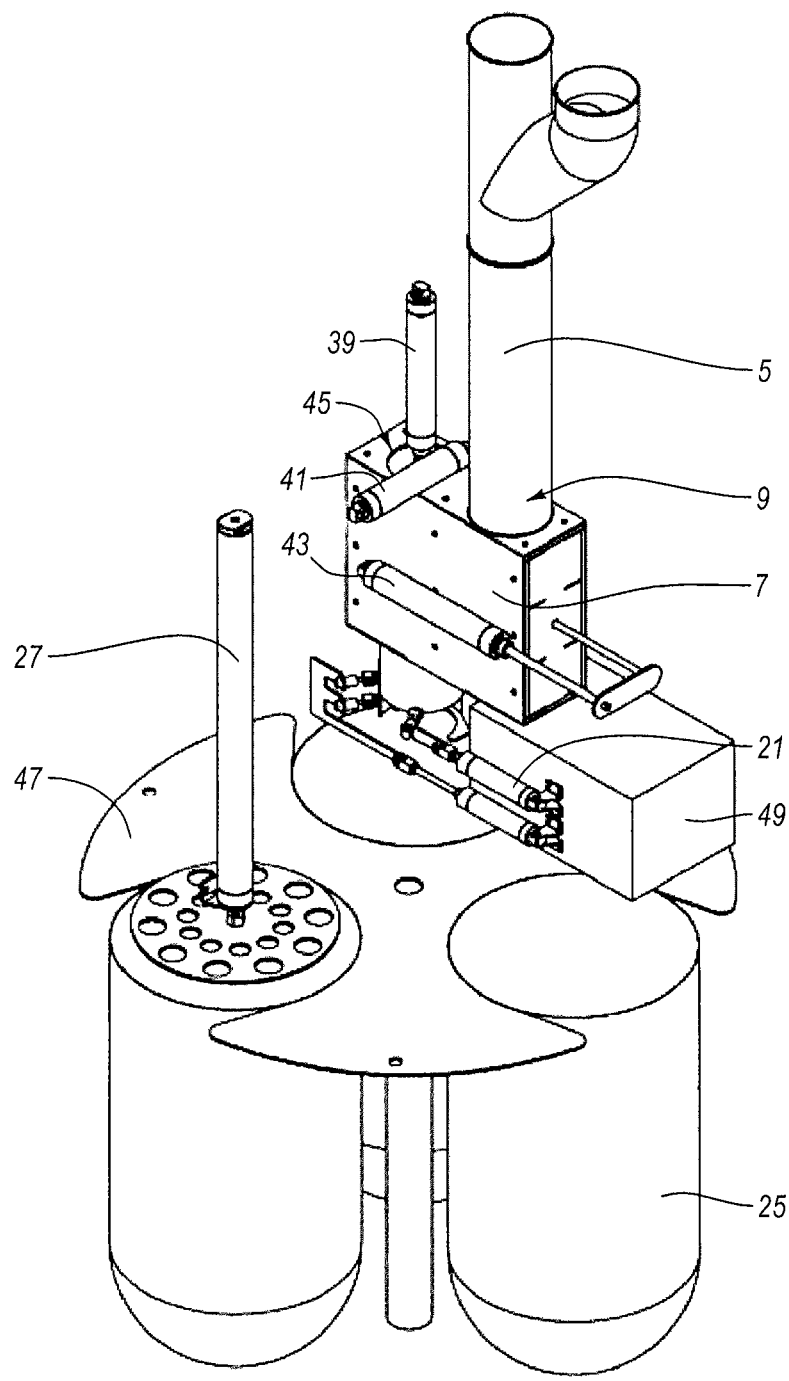
FIG. 15 shows a isometric view of the cotton sample receiver assembly of the cotton sample wrapping apparatus according to the other embodiment.
Figure 16:
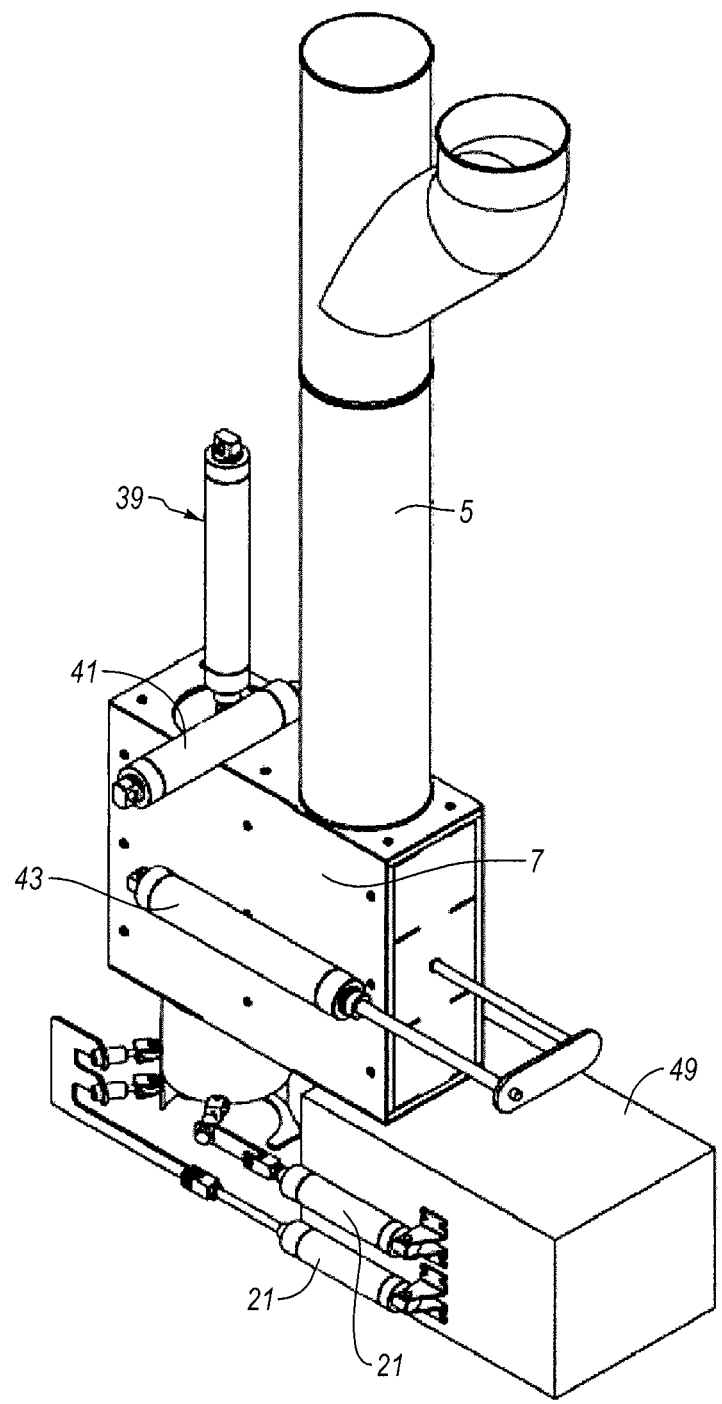
FIG. 16 shows another isometric view of portions of the cotton sample receiver assembly of the cotton sample wrapping apparatus according to the other embodiment.
Figure 17:
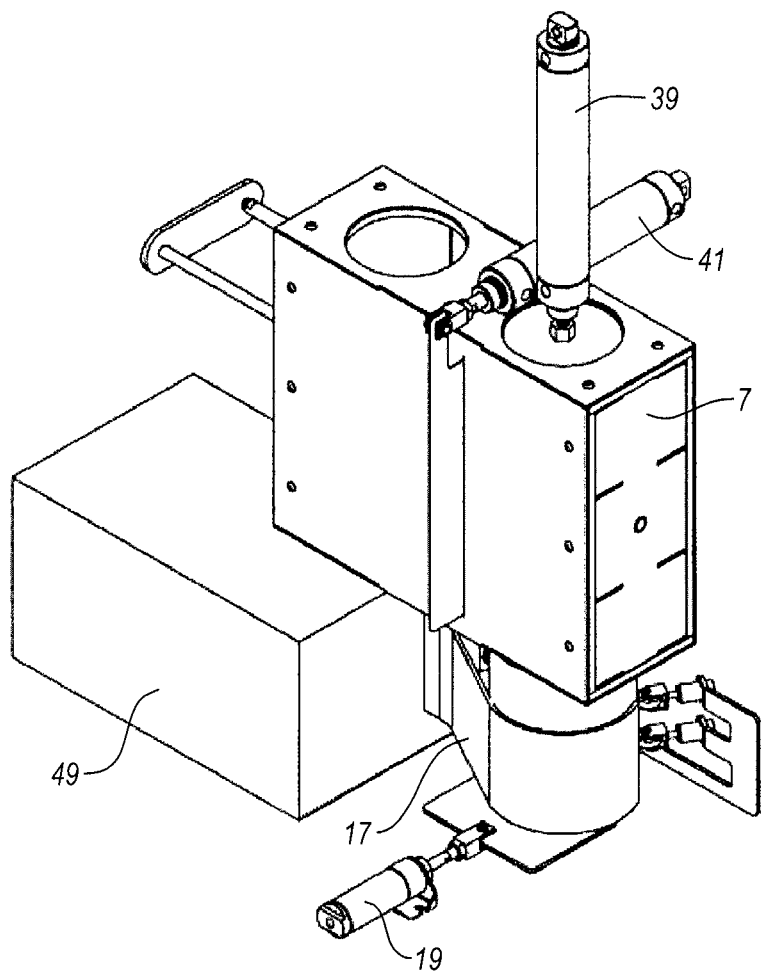
FIG. 17 shows another isometric view of portions cotton sample receiver assembly of the cotton sample wrapping apparatus according to the other embodiment.
Figure 18A:
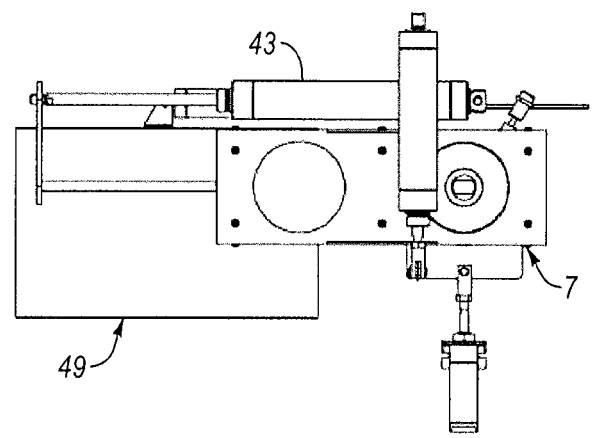
FIG. 18(a) shows a top view of portions of the cotton sampler receiver assembly of cotton sampling right side isometric view of a cotton sample wrapping apparatus according to the other embodiment.
Figure 18B:
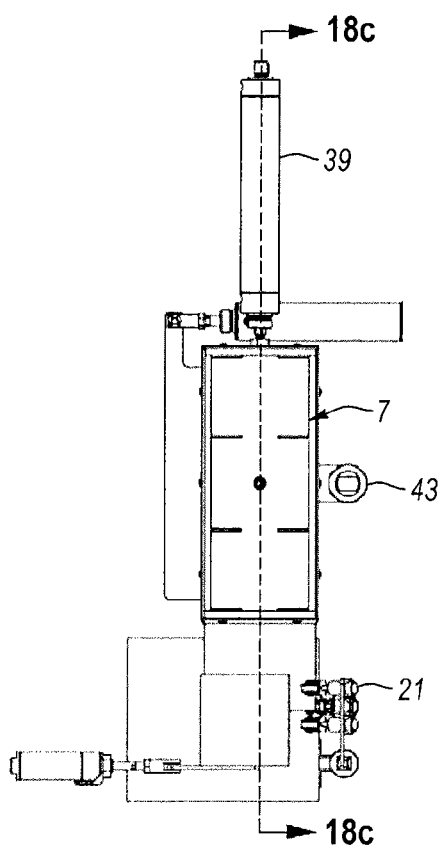
FIGS. 18(b) and 18(c) show a cross section view of the portions of the cotton sample receiver assembly illustrated in FIG. 18(a).
Figure 18C:
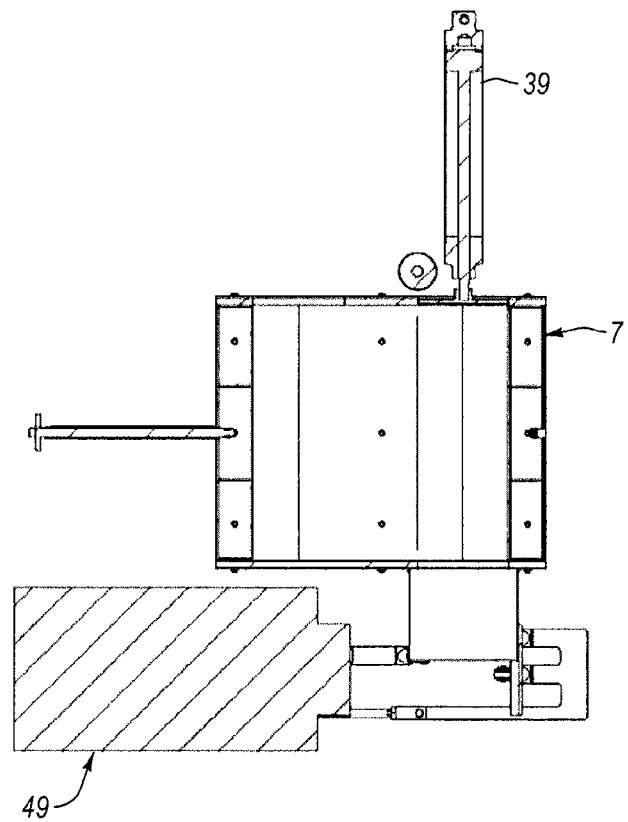

The collection device 18 is also provided with a slot 38 near the curved portion 36 for receiving printed information from the printing station 20. The printing station 20 is a standard labeling machine as known in the art to make tags and is configured to receive information used to identify the cotton bale sample with the cotton bale from which the sample was taken. For example, a unique eye readable number, i.e., a 12 digit identification number, and standard scannable barcode from the PBI is concurrently transmitted to the bale labeling station 12 and the printing station 20 so that the cotton bale sample has the same or similar identification number and bar code to associate the sample with the bale. The skilled person would appreciate that other identifying information can also be used to match the sample with the bale, including ginning address, gin code, etc. as known in the art. This information 60 is then printed on the rolls of adhesive labels 40, an example of which is shown in FIG. 10.

As further seen in FIGS. 5-6(*b*), the compacting device 22 is connected to a track 42 and a compacting device actuator 44 where the track 42 and compacting device actuator 44 are configured to move the compacting device 22 towards and away from the collection device for engagement and disengagement with the collection device 18 through the second opening 32. The track 42 is a track as well known in the art for moving the compacting device 22, for example, a rack and pinion, conveyor, or pulley operated configuration. In this embodiment, the compacting device is a rolling device having a roller motor 46 having pins 48 that extend away from the roller motor 46, where the pins 48 are configured to engage the sample sections that are partially rolled by the curved portion 36 of the collection device 18. The skilled person, however, would appreciate that the compacting device 22 can be any device used to at least partially compress or compact the sample section or sections to allow the subsequent wrapping of the elongate substrate around the cotton bale sample.

The roller station also includes a pushing plate 50 connected to a pushing actuator 52 mounted on a top portion of the compacting device 22, which are configured to remove the rolled sample from the pins 48 of the roller motor 46. For example, when the compacting device 22 is in a retracted position, which pulls the rolled sample from the collection device 18, the pushing plate 50 is configured to push the wrapped cotton bale sample having the proper identification information printed on the adhesive label from the pins 48 of the roller motor 46 into a gap having a bag provided for shipping the collected samples to the USDA.

B. Discussion of Various Methods of Operation for Securely Fastening Identification Information on the Sample An exemplary method for preparing a cotton bale sample having identification information in accordance with the present invention will now be described in detail below with reference to FIGS. 7-10.

Figure 7:
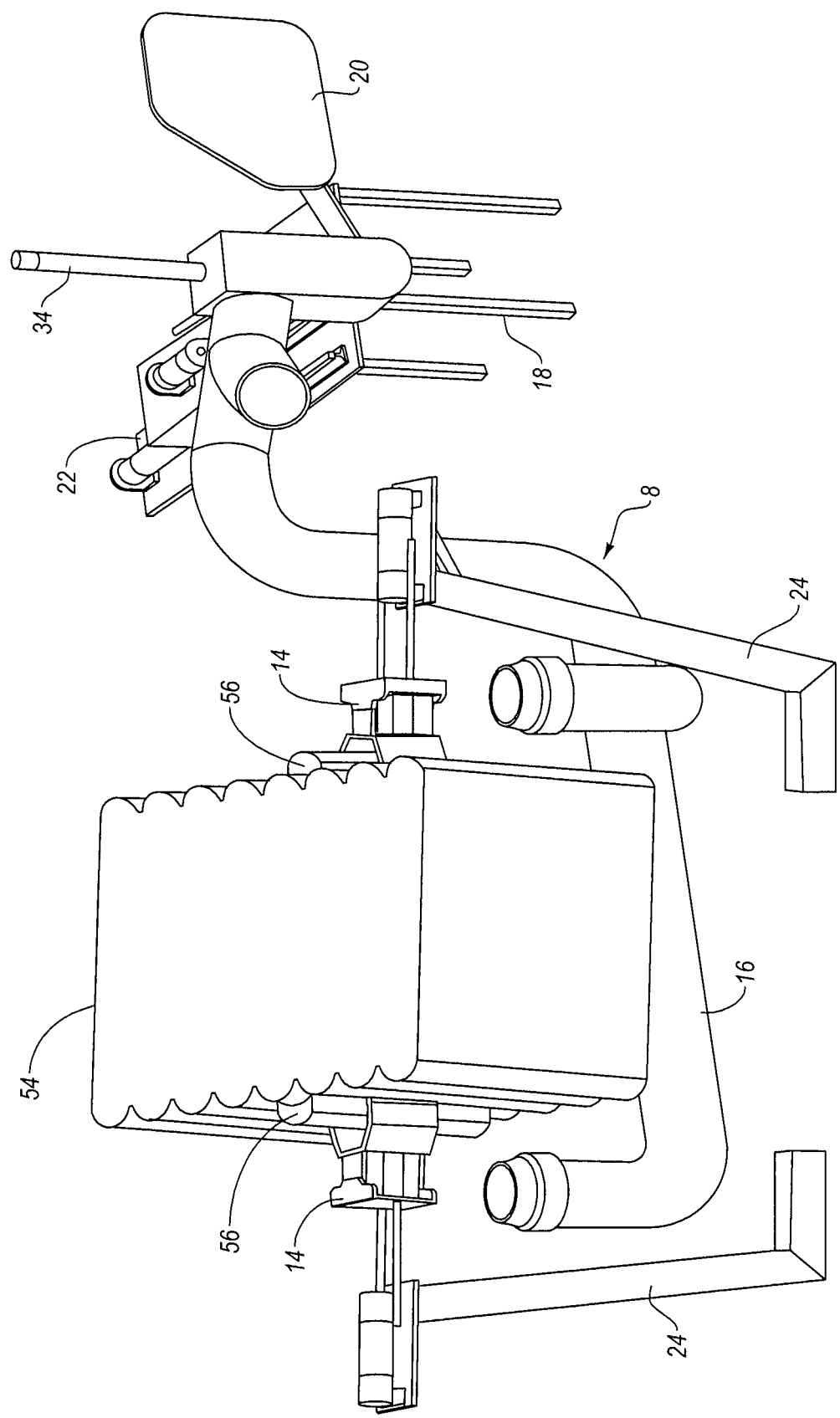
FIG. 7 shows a right side isometric view showing the removing of the samples from a cotton bale positioned at the sampling station of FIG. 2.

FIG. 7 shows a bale of cotton 54 having typically two cut portions or sample sections 56 protruding from at least two opposing sides of the cotton bale 54. Once the cotton bale 54 is located at the sampling station 8, opposed grippers 14 are aligned to engage and remove the cut portions of the cotton bale 54 to form at least two sections of a cotton bale sample 58.

Figure 8:
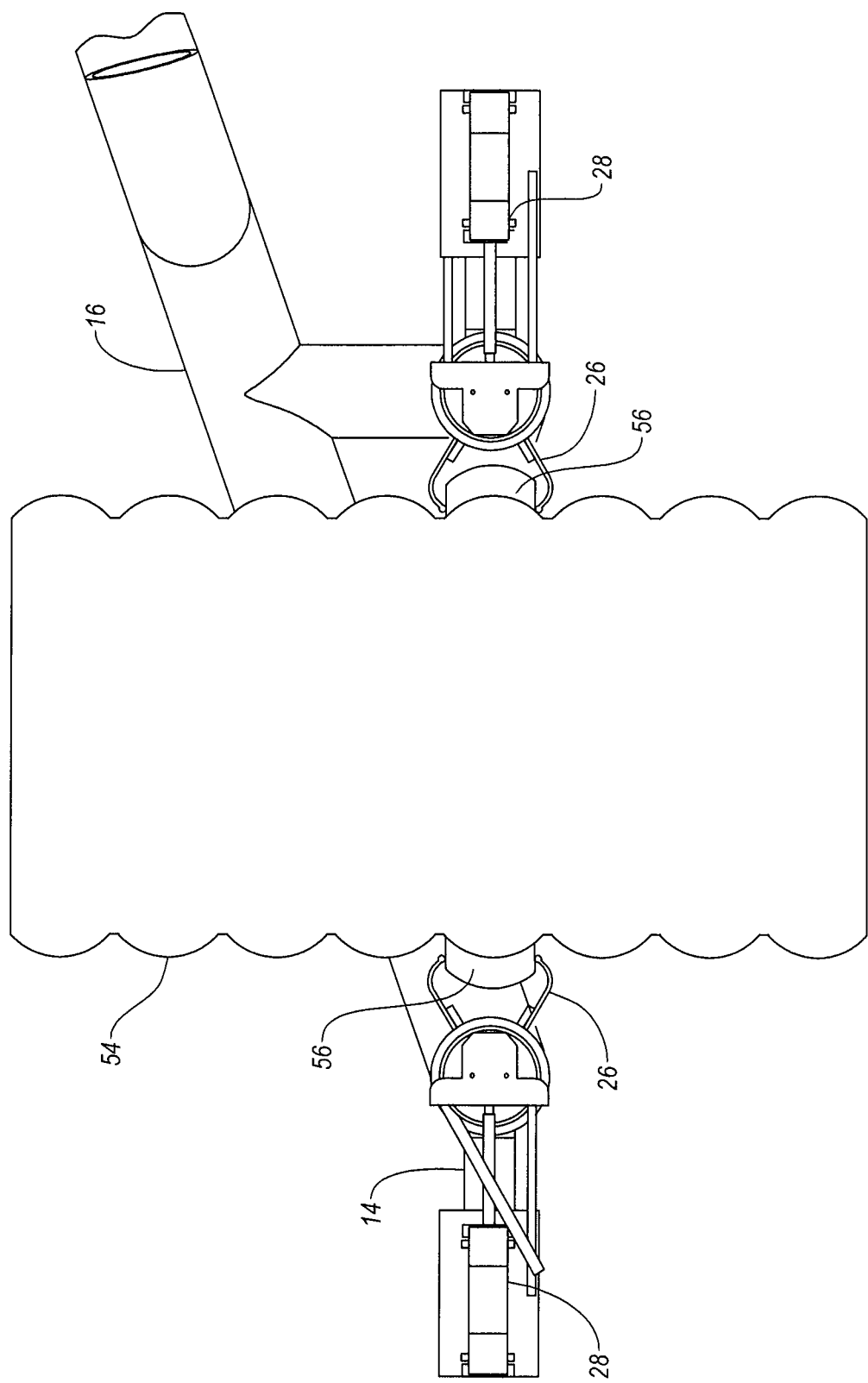
FIG. 8 shows a top side view of the removing of the samples of FIG. 7.

As seen in FIG. 8, after the grippers 14 remove the sample sections 56, they are aligned to be deposited into the pneumatic transport system 16. The pneumatic transport system 16 is then used to transport the sample sections 56 to the collection device 18 using a vacuum pump (not shown) arrangement.

When the sample sections 56 are deposited into the collection device 18, the plunger 34 is used to push the sections towards the curved portion 36 of the collection device 18. As the sections 56 are pushed along the curved portion 36, they start to form a rolled singular sample 58 (FIG. 9) having the geometry of the curved portion 36.

The compacting device 22 is then moved along the track 42 by actuation of the compacting device actuator 44 to engage the second opening 32 of the collection device 18 so that the pins 48 of the roller motor 46 engage the cotton bale sample 58. As the roller motor 46 rotates, the pins 48 engage the cotton bale sample 58 to roll the sample to form a compacted, rolled sample. During the rolling of the cotton bale sample, the printed adhesive label 40 having the identification information label 60 thereon to associate the cotton bale sample 58 with the cotton bale from which the sample was taken is fed into the slot 38 of the collection device 18 so that the adhesive label 40 with bale information 60 is wrapped completely around the rolled sample 58. The label is wrapped over the sample until the ends of the label 40 overlap and then the ends of the label are adhesively affixed together leaving the bale information in full view.

Optionally, the adhesive label 40 can also have a weakened tear zone (not shown) near its end areas to allow the subsequent removal of the adhesive label 40 from the cotton bale sample by tearing to avoid damaging or defacing the identification information 60. The adhesive label 40 may include an adhesive along the entire length of the label facing the cotton sample.

After the cotton bale sample 58 is compacted, i.e., rolled, and securely fastened by wrapping the adhesive label 40 with the identification information 60 completely around the cotton bale sample, the compacting device 22 is actuated by controlling the compacting device actuator 44 to disengage from the collection device 18, which results in the rolled cotton bale sample 58 being removed from the collection device 18 due to their engagement from being rolled around the pins 48. The pushing plate 50 is then actuated by activating the pushing actuator 52 to push the rolled cotton bale sample 58 from the pins 48 into a gap (not shown) for depositing the sample into a bag for USDA delivery.

Figure 9:
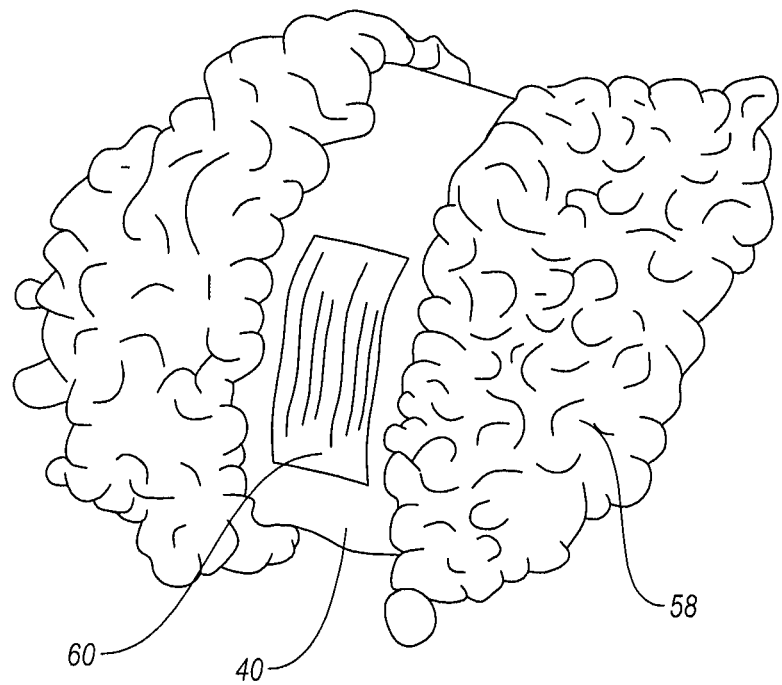
FIG. 9 shows a sample having an adhesive label wrapped completely around the sample.

As seen in FIG. 9, the cotton bale sample 58 is prepared by wrapping the adhesive label 40 completely around the sample, where the adhesive label 40 includes identification information 60. The adhesive label 40 is used to wrap the sample 58 to keep the sample sections 56 together up to the classification and grading process, so that the proper identification of the sample can be maintained throughout the process. After wrapping, the cotton material of the sample will naturally expand on opposite sides and partially around the label 40 due to natural resiliency of the cotton (see FIG. 9), and this expansion against and around the band will keep the band securely on the sample during transit and processing.

While a single exemplary embodiment and method for preparing a cotton bale sample with identification information has been described, the method and apparatus could be implemented in various ways and forms without departing from the novel concepts underlying the invention. Specifically, as described above in its broadest aspect, the method for preparing a cotton bale sample includes the steps of removing at least one section from a cotton bale and wrapping an elongate substrate having bale identification information completely around the section to associate the sample with the bale. While the above described method recites a particular order of steps, the skilled person will appreciate that any order of operation can take place to allow the preparation of the sample.

For instance, the adhesive label 40 can be positioned along the curved portion 36 before the collection device receives the sample sections 56, so that when the sample 58 is positioned and rotated using the pins 48, the adhesive label 40 is already in place for wrapping the sample.

The skilled person will also appreciate that any suitable apparatus can be used to carry out the steps for wrapping a band with bale identification information around a cotton bale sample. The specific apparatus and method steps discussed above are thus intended to describe examples of mechanisms and process steps that could be used. For example, while a roller motor with pins is discussed above with respect to the compacting device, any known compacting device can be used to collect and join the two sample sections (assuming two sections are extracted from a bale) from the bale to allow the subsequent wrapping and fastening of a band (generally referred to herein as an elongate substrate) having identification information completely around the sample.

As regards to the grippers of the sampling station, the skilled person will also appreciate that although only one set of grippers on each side of the conveyor system is shown and described, multiple sets of grippers which are aligned vertically can also be used. When using the multiple set of grippers aligned vertically, the grippers are used to grasp the top and bottom halves of the cut portion of the bale to collect two sample sections, thereby providing a more efficient system for obtaining the sample sections over the entire length of the cut portion.

Additionally, although the figures illustrate that the grippers are positioned in-line with each other, i.e., across from each other, the skilled person will appreciate that the grippers can also operate independently. In such a case, one gripper is configured to grasp, i.e., remove, the cut portion at a first time in a first position on the conveyor, and the second gripper may cut a portion of the bale at a second later time with the bale at a second position on the conveyor.

Furthermore, although FIG. 5 illustrates the printing of identification information 60 on rolls of adhesive labels 40, the skilled person will appreciate that other banding devices using elongate printable substrates can be used for wrapping around the cotton bale samples. For example, the printable substrate can be metal banding strips, paper, plastic substrates, elastic polymers, or combinations thereof that use fastening means such as adhesive, buttons, hook and loops, clasps or other fastening devices that are used to secure the ends of the elongate substrate in position around the cotton bale sample. Alternatively, the elongated substrate may include a band designed to self-fasten, such as die-cut paper. If a printed substrate is used, printing may be implemented by using known printing techniques, for example, laser printing, engraving, embossing, etching, ink printing, etc. The labels may be provided with or without an adhesive, such as in pre-made bands. Band ends may be fastened to one another, and formed from a die-cut paper.

The resulting cotton bale sample 58 then is seen to constitute one or more sections of a compressed bale of cotton wrapped with an elongate substrate or band having bale information thereon that associates the sample with the bale. The band can be in different forms and the sample may be compacted somewhat during the wrapping process to result in the cotton of the sample expanding around and against the band to securely hold the band and sample together. Various forms of substrates are envisioned, with various forms of securing the substrate around the sample and applying the information to the substrate are envisioned as well. The thus wrapped sample is ready for packaging and transport to a certification authority while being maintained in a compact, securely wrapped condition.

As shown in FIGS. 11 to 18(c), in another embodiment, a cotton sample wrapping apparatus is designed to accept cotton bale samples from either a pneumatic conveying system (not shown) including a sample delivery conduit 5 or manual feed system (not shown). An operator interfaces with the sampling system through an operator interface panel 37. One or more cotton bale samples can be transferred to the automatic sample receiver assembly 7 as either single cotton bale samples or an aligned pair of cotton bale samples.

Figure 19A:
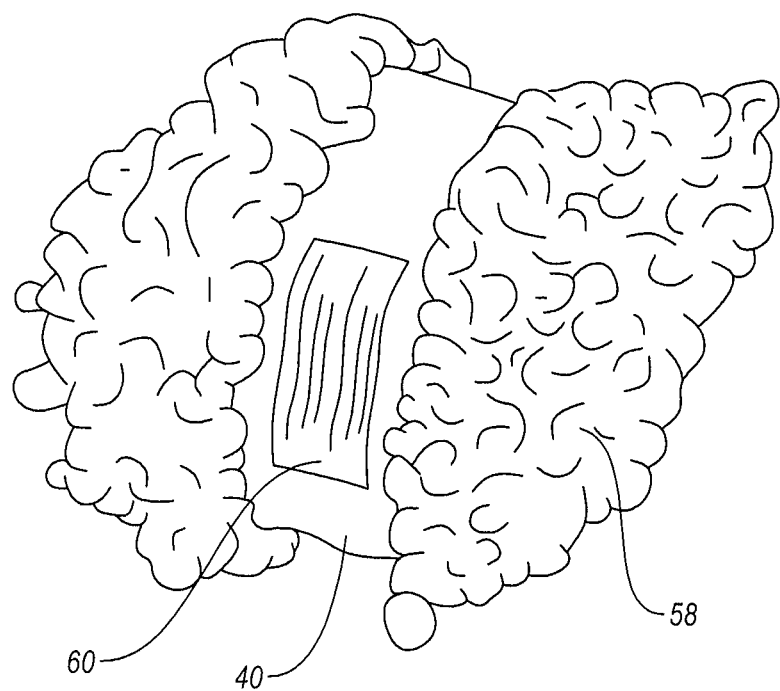
FIGS. 19(a) and 19(b) show a cotton bale sample according to the other embodiment, FIG. 19(a) showing an isometric view of the cotton sample and FIG. 19(b) showing a side view of the cotton sample.
Figure 19B:
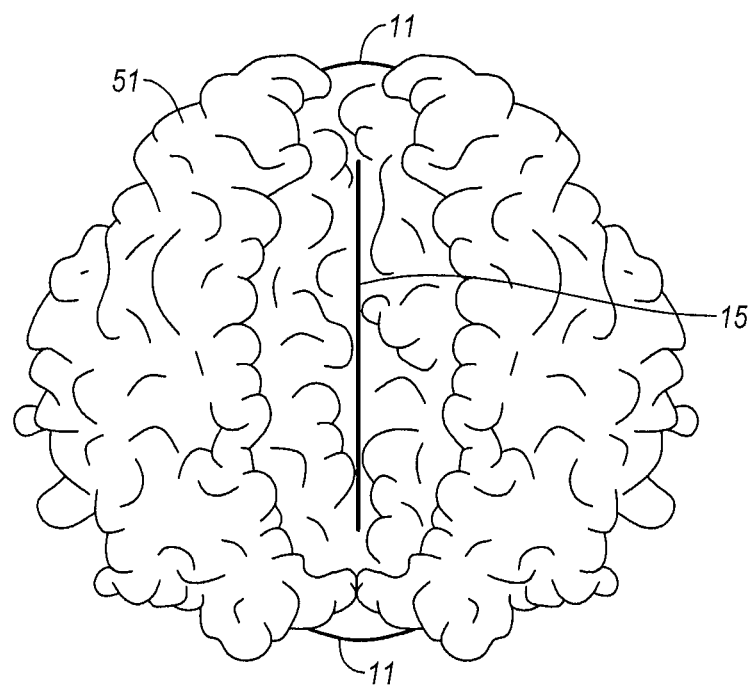

When transferred a single cotton bale sample will enter the automatic sample receiver assembly inlet 9 and rest against the sample receiver baffle (not shown) attached to the sample receiver baffle actuator 41. The sample receiver baffle actuator 41 will then open to allow the cotton bale sample receiver tramper actuator 43 to transfer a first cotton bale sample into the plunger section 45 of the receiver. The cotton bale sample receiver tramper actuator 43 then returns to its starting position as does the sample receiver baffle actuator 41. A second cotton bale sample can now be transferred and the process of moving the cotton bale sample to the plunger section of the automatic sample receiver assembly 7 is repeated. During the second sample transfer in the sample receiver, it is optionally possible to use the device for storing, advancing, and inserting a substrate 15 with unique identification number between the first and second cotton bale sample portions 13, resulting in a cotton bale sample 51 according to the other embodiment, as shown in FIGS. 19(a) and 19(b).

With the two cotton bale samples now securely in the plunger section of the automatic sample receiver assembly the system is commanded by the code instructions in the programmable logic controller (PLC) to use bale identification information automatically read off the corresponding cotton bale and transmitted to the device 49 for placing unique identification information 53 on an elongated substrate 11. Once the matching information has been placed on the elongated substrate 11 and verified, the elongated substrate 11 is then transferred to the device 17 for cutting the elongated substrate 11 (if configured with elongated substrate as roll stock). The elongated substrate 11 is then moved to the device 19 for advancing the elongated substrate 11 into the wrapping position. The elongated substrate 11 is moved into a device 21 for connecting the ends of the elongated substrate 11 (for example, lapping one end over the other end at a specific time and overlap distance). The device actuates and creates a band or wrapper around the discharge port 23 on the sample receiver assembly 7. The device 21 for connecting the ends of the elongated substrate 11 has the potential to aid in the positioning of the band or wrapper of the elongated substrate 11 along the combined cotton bale samples length.

With the band or wrapper positioned at the discharge port 23 the cotton bale sample receiver plunger actuator 39 moves the combined sample out of the plunger section of the receiver assembly through the discharge port 23. The device 21 for connecting the ends of the elongated substrate 11 releases at such time so as to band or wrap the combined cotton bale sample at or near the midpoint of the sample. (A premade band or wrapper can be placed on the discharge port 23 of the sample receiver assembly 7.)

The banded or wrapped sample 51 is discharge into the device for receiving and collecting wrapped cotton bale samples into USDA approved master package 25. As shown in FIGS. 19(a) and 19(b), the banded or wrapped sample 51 may optionally include an inserted substrate 15 between a first cotton bale sample and the second cotton bale sample, the first and second cotton bale samples being bound or wrapped together by elongated substrate 11.

Once the device for receiving and collecting wrapped cotton bale samples into USDA approved master package 25 collects a known quantity of banded or wrapped samples 51 the cotton bale sample receiver tramper actuator 43 cycles and compacts the samples in the USDA approved master package 25. Once the samples in the USDA approved master package 25 have been through the compacting cycle the device for stowing and indexing USDA approved master package 47 can be actuated either automatically or manually to present an empty USDA approved master package 25 at the discharge port 23 of the sample receiver assembly 7.

According to the above described embodiments, the elongated substrate can be designed so as to minimize the material required for connecting two cotton bale samples. Secondarily the elongated substrate can be designed so that the portion of the substrate that is needed to meet USDA unique identification requirements can be removed easily (i.e. perforated substrate section or peel off). Thirdly the elongated substrate material can be made of any of a wide range of materials in order to meet physical size requirements for the combined sample or to utilize particular substrate properties (i.e. recycled or elastic). Finally the elongated substrate surface area can be minimized so as to meet both identification requirements on the substrate while minimizing the restriction of airflow through the samples which is a critical conditioning step in the USDA inspection process. By minimizing the restriction to airflow while providing a means to unitize and integrate the two cotton bale samples it is possible for USDA classing offices to move unitized samples automatically through the conditioning stages of their inspection process.

Placing a breathable label on the outside of the bale sample makes improvements to practices in the cotton baling industry. These include, but are not limited to, securing the tag information to the bale sample in an integrated manner, rather than loose where it can be lost and improves the breathability of the bale sample. The identification information can be scanned when received (if desired) without separating the two halves the sample often comprises. This would improve traceability of the sample. The above described examples also allow for automation of handling and packaging of the sample half's for shipment at the cotton gin and handling of the sample at the USDA. The identification information being on the outside, where it can be read without being handled by hand, provides many opportunities for automation of processing equipment at the USDA.

The embodiments described above show how a label may be applied. The label, or elongated substrate including identification information, may be of various sizes and shapes, or perforated material to improve breathability or a printed label. The label could be from roll stock or pre-formed bands. However, although these and other various elongated substrates that could be used and various means may be used to apply the label to the removed portion, an elongated substrate is used to wrap around the sample, the elongated substrate including identification information associating the sample bale with the bale. Preferably the label is of a size and breathability to allow the sample to be conditioned in the USDA existing system without having to remove the label from the sample.

Although the above embodiments describe samples taken from a cotton bale, the disclosure is not limited to sampling a cotton bale, but can be equally applied to sampling a bale of any fibrous material, for example a bale of agricultural products, such as, but not limited to, wool, cotton, hemp, flax, etc., or other fibrous materials, either naturally or synthetically produced, that may be sampled for various purposes. Such purposes can include, but are not limited to, analysis by a government agency, such as a division of the U.S. Department of Agriculture (USDA), or any other inspecting or certifying body.

The foregoing description of exemplary forms or embodiments of methods and apparatus for securely fastening identification information around a bale sample and a sample produced thereby is not intended to limit the scope of the present invention in any manner beyond the full scope of the appended claims.

What is claimed:

1. A method for preparing a cotton bale sample, the method comprising the steps:
   removing two or more portions from a cotton bale, wherein the cotton bale is pre-cut at least at a first location and a second location, and the portions removed from the cotton bale include at least a first cut section removed from the first location and a second cut section removed from the second location;
   joining the first cut section and the second cut section together to form a bale sample; and
   wrapping an elongated substrate completely around the bale sample to form a wrapped bale sample, wherein the elongate substrate includes an adhesive band, and the step of wrapping the elongated substrate includes
      wrapping the adhesive band around the bale sample, and
      joining free ends of the adhesive band together while the portions are in a more compacted condition than when the portions are removed from the cotton bale, the elongated substrate having a width less than the width of the wrapped bale sample, the width of the elongated substrate being substantially perpendicular to the direction in which the elongated substrate is wrapped around the bale sample such that the wrapped bale sample includes a compressed banded portion between a first exposed end portion and a second exposed end portion, the first exposed end portion and the second exposed end portion being not covered by the elongated substrate,
   wherein the elongated substrate includes identification information, and
   wherein the identification information includes information that associates the bale sample with the bale.

2. The method according to claim 1, further comprising a step of compacting the portion to a more compacted condition than when the portion is removed from the bale, the step of compacting being performed prior to the wrapping step.

3. The method according to claim 2, wherein the compacting step includes rolling the portion at a collection station to form a rolled section prior to the wrapping step.

4. The method according to claim 1, including bagging the wrapped bale sample for transport.

5. The method according to claim 1, wherein the removing step includes transporting the portion to a collection station using a transport system.

6. The method according to claim 5, wherein the transport system includes a pneumatic transport system in which the portion that is removed is transported through a pneumatic tube.

7. The method according to claim 1, wherein the identification information provided on the elongate substrate includes at least one of a scannable bar code and a unique eye-readable bale identifier that associates the cotton bale sample to the cotton bale.

8. The method according to claim 1, wherein the cotton bale is pre-cut on at least two opposing sides of the bale to form at least first cut section and the second cut section, the first cut section and the second cut section being joined together at a collection station before wrapping the sections with the elongate substrate.

9. The method according to claim 1, further comprising inserting a substrate between a first section of the portion and a second section of the portion, the substrate being secured between the first and the second sections of the portion upon wrapping the elongated substrate around the portion,
   wherein the substrate includes unique identification information corresponding to the cotton bale.

10. The method according to claim 1, wherein the step of wrapping is performed as the portion is discharged from a portion receiver, the portion receiver including a plunger section configured to compress the portion.

11. The method according to claim 1, wherein the elongated substrate includes a breathable material.

12. A cotton bale sampling apparatus comprising:
   a portion removing device configured to remove two or more portions from a cotton bale, wherein the cotton bale is pre-cut at least at a first location and a second location, and the portions removed from the cotton bale include at least a first cut section removed from the first location and a second cut section removed from the second location;
   a collection station configured to join the first cut section and the second cut section together to form a bale sample;
   a wrapping station configured to wrap an elongated substrate around bale sample to form a wrapped bale sample, wherein the elongate substrate includes an adhesive band, and the wrapping station wraps the elongated substrate by
      wrapping the adhesive band around the bale sample, and
      joining free ends of the adhesive band together while the portions are in a more compacted condition than when the portions are removed from the cotton bale, the elongated substrate having a width less than the width of the wrapped bale sample, the width of the elongated substrate being substantially perpendicular to the direction in which the elongated substrate is wrapped around the bale sample such that the wrapped bale sample includes a compressed banded portion between a first exposed end portion and a second exposed end portion, the first exposed end portion and the second exposed end portion being not covered by the elongated substrate,
   wherein the elongated substrate includes identification information, and
   wherein the identification information includes information that associates the bale sample with the cotton bale.

13. The apparatus according to claim 12, further comprising a compacting station configured to compact the portion, after the portion is removed, to a more compacted condition than when the portion is removed from the cotton bale.

14. The apparatus according to claim 13, wherein the compacting station includes a rolling device configured to rotate along an axis and pins connected to the rolling device, the pins extending away from the rolling device and configured to engage and roll the portion into a rolled bundle about the axis.

15. The apparatus according to claim 12, wherein the portion includes at least two cut section, the cut sections being pre-cut from at two opposing sides of the cotton bale, and the cut sections are joined together at a collection station before wrapping the sections with the elongate substrate.

16. The apparatus according to claim 12, further comprising a substrate inserting device configured to insert a substrate between a first section of the portion and a second section of the portion, the substrate being secured between the first and the second sections of the portion upon wrapping the elongated substrate around the portion,
   wherein the substrate includes unique identification information corresponding to the bale.

17. A cotton bale sample comprising:
   two or more portion removed from a cotton bale,
   wherein the cotton bale is pre-cut at least at a first location and a second location, and the portions removed from the cotton bale include at least a first cut section removed from the first location and a second cut section removed from the second location, and the first cut section and the second cut section are joined together; and
   an elongate substrate wrapped completely around the joined portions to form a wrapped bale sample,
   wherein the elongate substrate includes an adhesive band, and the elongated substrate is wrapped around the joined portions such that free ends of the adhesive band are joined together while the portions are in a more compacted condition than when the portions were removed from the cotton bale, the elongated substrate having a width less than the width of the wrapped bale sample, the width of the elongated substrate being substantially perpendicular to the direction in which the elongated substrate is wrapped around the portions such that the wrapped bale sample includes a compressed banded portion between a first exposed end portion and a second exposed end portion, the first exposed end portion and the second exposed end portion being not covered by the elongated substrate,
   wherein the elongate substrate including identification information, and
   wherein the identification information includes information that associates the bale sample with the cotton bale.

* * * * *